United States Patent [19]

Cohen et al.

[11] 4,426,535

[45] Jan. 17, 1984

[54] METHOD OF SYNTHESIZING BREVICOMIN AND USING SAME IN BEETLE CONTROL

[75] Inventors: Theodore Cohen, Pittsburgh, Pa.; James Matz, Ithaca, N.Y.

[73] Assignee: University of Pittsburgh, Pittsburgh, Pa.

[21] Appl. No.: 312,988

[22] Filed: Oct. 20, 1981

[51] Int. Cl.³ ............................................ C07D 311/00
[52] U.S. Cl. ................................... 549/397; 549/355; 549/363
[58] Field of Search ........................ 549/355, 397, 363

[56] References Cited

U.S. PATENT DOCUMENTS

| 2,511,890 | 6/1950 | Whetstone et al. | 260/338 |
| 2,511,891 | 6/1950 | Whetstone et al. | 260/338 |
| 2,980,703 | 4/1961 | Dunlop et al. | 549/397 |
| 3,755,365 | 8/1973 | Fentiman et al. | 260/340.9 |
| 3,755,563 | 8/1973 | Vite | 424/84 |
| 3,828,075 | 8/1974 | Dietl | 260/340.9 |

FOREIGN PATENT DOCUMENTS 646829 11/1950 United Kingdom .

OTHER PUBLICATIONS

Vite and Renwick, "Inhibition of Dendroctonus Frontalis Response to Frontalin by Isomers of Brevicomin" 58 Naturwissenschaften, p. 418 (1971).

*Primary Examiner*—Ethel G. Love
*Attorney, Agent, or Firm*—Buell, Blenko, Ziesenheim & Beck

[57] ABSTRACT

A method of producing synthetic brevicomin by direct distillation and a method of using the same in interfering with normal propagation of Dendroctonus beetles.

12 Claims, No Drawings

METHOD OF SYNTHESIZING BREVICOMIN AND USING SAME IN BEETLE CONTROL

The invention described herein was made in the course of work under a grant or award from the Department of Health and Human Services.

BACKGROUND OF THE INVENTION

1. Field of the Invention

This invention relates to a method of producing synthetic brevicomin and, more specifically, it relates to such a method involving direct distillation as well as use of the same in beetle control.

2. Description of the Prior Art

In prior methods of producing synthetic brevicomin it has generally been necessary to employ time consuming chromatographic separation techniques which were not adapted for larger scale, economic production.

It has previously been recognized that brevicomin can be employed advantageously in connection with controlling reproduction of the southern pine beetle (*Dendroctonus frontalis* Zimm.) and the western pine beetle (*Dendroctonus brevicomis* LeConte). See U.S. Pat. Nos. 3,755,563 and 3,755,365. See also the Vite and Renwick, 58 Naturwissenschaften page 418 (1971). Also, see as general background U.S. Pat. Nos. 2,511,890, 2,511,891, British Pat. No. 646 829 and U.S. Pat. No. 3,828,075.

In spite of these prior teachings there is lacking a teaching of an effective, economically feasible means for synthetic production of brevicomin which does not involve the use of poisonous materials or chromatographic separations.

SUMMARY OF THE INVENTION

The present invention has met the above described needs by providing a means for direct distillation production of brevicomin and, more specifically, the isomers endo-brevicomin and exo-brevicomin.

In the method of the present invention a reactive metal reducing agent such as lithium 1-(dimethylamino)naphthalenide is admixed with an alpha-(phenylthio) ether substrate. The resultant solution is admixed with propionaldehyde and the reaction mixture is diluted with three times its volume of ether. After washing the residue is distilled to provide a mixture consisting of exo-brevicomin and endo-brevicomin.

The brevicomin may then advantageously be distributed in regions where beetle control is desired such as by local placement in appropriate traps or by spraying.

It is an object of the present invention to provide an economical, rapid means of synthesizing endo-brevicomin and exo-brevicomin.

It is a further object of the present invention to provide such a method which does not employ toxic reagent materials.

It is another object of the present invention to provide a method of direct distillation production of brevicomin.

These and other objects of the invention will be more fully understood from the following description of the invention.

DESCRIPTION OF THE PREFERRED EMBODIMENTS

The present invention contemplates a two step, direct distillation method of producing the isomers endo-brevicomin and exo-brevicomin. While the invention is not so limited, in one preferred use, the improved synthesis of the present invention will permit ready and economical commercial adoption of brevicomin as a material for use in control of the aggregation behavior of the western pine beetle, the southern pine beetle and the douglas fir beetle (*Dendroctonus pseudotsugae*, Hopk.). Both isomers are exuded by the female western pine beetle and the exo-isomer is a key component in its aggregation pheromone. The endo-isomer is a potent inhibitor of the aggregation behavior of the southern pine beetle.

In a preferred method of practicing the present invention a substrate is produced from phenyl vinyl sulfide and methyl vinyl ketone. A reducing agent is provided in the form of lithium 1-(dimethylamino)naphthalenide and after suitable processing, distillation will yield a mixture of the two isomers.

In a preferred method of practicing the invention a reactive metal reducing agent will be provided in solution form. The reducing agent is preferably selected from the group consisting of lithium 1-(dimethylamino)-naphthalenide, lithium naphthalenide, lithium biphenylide and similar radical anions. The preferred reactive metals for use in providing a reducing agent are selected from the group consisting of lithium, sodium potassium and calcium.

The reactive metal reducing agent is admixed with an alpha-(phenylthio) ether substrate. It is preferred to employ a minimum of about 2.0 moles of the reducing agent per mole of the substrate. The reducing agent and substrate are preferably then admixed at about $-40°$ C. to $-93°$ C. for about 15 to 90 minutes. Subsequently, about 1 to 10 moles and preferably about 1½ to 5 moles of propionaldehyde is added and stirring is continued to about 5 to 15 minutes. The reaction mixture is then diluted with about two to four times its volume of ether and the whole is washed with water and subsequently with a dilute aqueous acid solution. An acid range of about 1 to 15% is preferred. Among the preferred acids are an acid selected from the group consisting of hydrochloric acid, sulfuric acid, perchloric acid, and tetraflouraboric acid. The solvent is then removed in vacuo from the dried (magnesium sulfate) organic layer and the residue is distilled to provide a mixture of the isomers exo-brevicomin and endo-brevicomin. Solvent removal may readily be accomplished by employing a rotary evaporation at about 0° C. It has been determined experimentally that the resultant mixture will consist of about 55 to 60% endo-brevicomin and about 40 to 45% exo-brevicomin.

Among the characterizing tests which can be employed to confirm the result are relative retention times of the two isomers on a Carbowax 20M GLC, $^1$H Nuclear Magnetic Resonance Spectrum of the mixture and the mass spectrum of each isomer obtained by combined gas chromatography mass spectrometry.

It is found in lieu of use of ether in the workup of the brevicomins other low boiling hydrocarbons such as, for example, pentane, hexane, cyclohexane or other suitable organic solvents such as ethyl acetate, chloroform and methylene chloride may be employed, if desired.

In preparing the substrate and the reactive metal reducing agent it would generally be preferred to prepare them independently for subsequent admixture. However, should it be desired, they can be prepared simultaneously in the same container with the reduction times being slightly longer.

EXAMPLE

In order to provide further guidance regarding the synthesis of the present invention a specific example will now be considered.

A preferred approach involves the Diels-Alder addition of phenyl vinyl sulfide and methyl vinyl ketone, treatment of the adduct with a reducing agent followed by trapping the anion with propionaldehyde.

The reactive metal reducing agent, lithium 1-(dimethylamino)naphthalenide is prepared in the form of a 0.50 molar stock solution. An equimolar mixture of lithium ribbon and 1-(dimethylamino)naphthalene in tetrahydrofuran (two liters of the latter per mole of either reactant) is created at $-45°$ C. until the dissolution of the lithium occurs. This generally will take about 3½ to 4 hours.

Preparation of the substrate in the form of 2-methyl-6-phenylthio-4H-5,6,-dihydropyran will now be considered. A sealed tube containing 1.90 g. (14.0 mmol) of phenyl vinyl sufide and 2.3 ml (29 mmol) of methyl vinyl ketone, 30 mg. of butylated hydroxytoluene (an inhibitor of radical polymerization of reactants) and 0.05 ml of diisopropylethylamine (an inhibitor of acid catalized polymerization of the reactants) is heated at about 160° C. for one hour. It is preferred to employ about ½ to 15 mg of the acid inhibitor per mmol of methyl vinyl ketone. Distillation of the contents of the tube at about 0.025 torr. (mmHg) yields the substrate compound in yields of about 22 to 43% of the phenyl vinyl sulfide charge. About ½ of the vinyl sulfide material is recovered unchanged in an earlier fraction and can be reused. This reaction can be performed at temperatures of about 60° C. to 200° C. but the yields tend to be lower at the extremes.

If desired other inhibitors of radical polymerization such as hydroquinone or 3-tert.-butyl-4-hydroxy-5-methylphenyl sulfide, for example, could be used. Also, other acid catalyzed polymerization inhibitors, such as a tertiary amine could be employed. While the addition of the inhibitor of acid catalyzed polymerization is not necessary, it is preferred as it tends to lead to more predictable yields.

To 4.0 ml (2.0 mmol) of the reactive metal reducing agent solution is added is 0.90 mmol of the substrate at $-78°$ C. After the resulting solution has been stored for about 45 minutes, propionaldehyde (1.3 mmol) is added and stirring is continued for about 10 minutes. The reaction mixture is then diluted with about three times its volume of ether and the entire mixture is washed twice with water and twice in a separating funnel with a 5% aqueous hydrochloric acid solution. The solvent is removed in vacuo from the dried (magnesium sulfate) organic layer and the residue distilled to provide a 40% yield of a mixture of exo-brevicomin (43%) and endo-brevicomin (57%) (b.p. 150°-155° C.).

The resultant product is in the form of a liquid. It may be employed in this form or admixed with a suitable solvent for use in distribution to control the dendroctonus beetles described above. This may advantageously be done by placing the material in a trap or spraying, for example.

It will therefore be appreciated that the present invention provides an effective means for synthesizing the isomers exo-brevicomin and endo-brevicomin without the use of poisonous materials, by direct rapid distillation, as distinguished from time consuming and cumbersome chromatographic procedures. All of this makes the material economical for use in beetle control or other desired uses.

While for purposes of simplicity of the disclosure herein specific reference has been made to use in beetle control, it will be appreciated that the present invention is adapted to provide effective and rapid means for synthesizing brevicomin regardless of the end use desired.

Whereas particular embodiments of the invention have been described above for purposes of illustration, it will be appreciated by those skilled in the art that numerous variations of the details may be made without departing the invention as described in the appended claims.

We claim:

1. A method of synthesizing brevicomin comprising:
   providing a reactive metal reducing agent in solution form,
   selecting said reactive metal from the group consisting of alkali metals and alkaline earth metals,
   admixing with said reducing agent in alpha-(phenylthio) ether substrate which is the Diels-Alder adduct of phenyl vinyl sulfide and methyl vinyl ketone,
   effecting said admixture at about $-45°$ C. to about $-93°$ C., for at least about 15 minutes, adding to said reducing agent-substrate solution about 1 to 10 moles of propionaldehyde, adding an organic solvent, and washing the reaction mixture with an aqueous acid solution.

2. The method of synthesizing brevicomin of claim 1 including selecting said reactive metal from the group consisting of lithium, sodium, potassium and calcium.

3. The method of synthesizing brevicomin of claim 2 including selecting said reactive metal reducing agent from the group consisting of lithium 1-(dimethylamino)-naphthalenide and lithium naphthalenide.

4. The method of synthesizing brevicomin of claim 1 including before said acid washing, washing the reaction mixture with water.

5. The method of synthesizing brevicomin of claim 4 including after said acid washing removing the solvent from the dried organic layer and distilling the residue to provide brevicomin.

6. The method of synthesizing brevicomin of claim 2 including said washing acid having a concentration of about 1 to 15 percent.

7. The method of synthesizing brevicomin of claim 6 including said substrate being 2-methyl-6-phenylthio-4H-5,6-dihydropyran.

8. The method of synthesizing brevicomin of claim 7 including adding to said substrate forming mixture prior to heating about ½ to 15 mg of an inhibitor of acid catalyzed polymerization of said reactants per millimole of said methyl vinyl ketone.

9. The method of synthesizing brevicomin of claim 8 including adding an inhibitor of radical polymerization in forming said substrate, and said inhibitor of radical polymerization including butylated hydroxytoluene.

10. The method of synthesizing brevicomin of claim 9 including said acid catalyzing polymerization inhibitor including diisoproplyethylamine.

11. The method of synthesizing brevicomin of claim 1 including forming said reactive metal reducing agent simultaneously with and in the same vessel as said substrate.

12. The method of synthesizing brevicomin of claim 1 including selecting said organic solvent from the group consisting of ether, pentane, hexane, cyclohexane, ethyl acetate, chloroform and methylene chloride.

* * * * *

UNITED STATES PATENT AND TRADEMARK OFFICE
CERTIFICATE OF CORRECTION

PATENT NO. : 4,426,535
DATED : January 17, 1984
INVENTOR(S) : Theodore Cohen and James Matz It is certified that error appears in the above-identified patent and that said Letters Patent is hereby corrected as shown below:

Column 1, line 19, "larger" should be --large--.

Column 2, line 26, "sodium potassium" should read --sodium, potassium--.

Signed and Sealed this

Twenty-fourth Day of April 1984

[SEAL]

Attest:

GERALD J. MOSSINGHOFF

*Attesting Officer*    *Commissioner of Patents and Trademarks*